US008748481B2

(12) United States Patent
Ueno

(10) Patent No.: US 8,748,481 B2
(45) Date of Patent: Jun. 10, 2014

(54) METHOD FOR TREATING GASTROINTESTINAL DISORDER

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 11/216,012

(22) Filed: Sep. 1, 2005

(65) Prior Publication Data

US 2006/0063830 A1 Mar. 23, 2006

Related U.S. Application Data

(60) Provisional application No. 60/606,521, filed on Sep. 2, 2004, provisional application No. 60/666,317, filed on Mar. 30, 2005, provisional application No. 60/666,593, filed on Mar. 31, 2005.

(51) Int. Cl.
*A61K 31/352* (2006.01)

(52) U.S. Cl.
USPC .......................................... 514/456; 514/892

(58) Field of Classification Search
None
See application file for complete search history.

(56) References Cited

U.S. PATENT DOCUMENTS

| | | | |
|---|---|---|---|
| 5,166,174 A | 11/1992 | Ueno et al. | |
| 5,225,439 A | 7/1993 | Ueno et al. | |
| 5,284,858 A | 2/1994 | Ueno et al. | |
| 5,317,032 A | 5/1994 | Ueno et al. | |
| 5,380,709 A | 1/1995 | Ueno et al. | |
| 5,428,062 A | 6/1995 | Ueno et al. | |
| 5,886,034 A | 3/1999 | Ueno et al. | |
| 6,265,440 B1 | 7/2001 | Ueno et al. | |
| 6,414,016 B1 | 7/2002 | Ueno | |
| 6,583,174 B1 | 6/2003 | Ueno et al. | |
| 6,610,732 B2 | 8/2003 | Ueno | |
| 6,956,056 B2 | 10/2005 | Ueno | |
| 6,982,283 B2 | 1/2006 | Ueno | |
| 7,064,148 B2 | 6/2006 | Ueno et al. | |
| 2003/0119898 A1 | 6/2003 | Ueno et al. | |
| 2003/0130352 A1 | 7/2003 | Ueno et al. | |
| 2003/0166632 A1 | 9/2003 | Ueno | |
| 2004/0138308 A1 | 7/2004 | Ueno et al. | |
| 2004/0235885 A1 | 11/2004 | Ueno et al. | |
| 2005/0222195 A1 | 10/2005 | Ueno | |
| 2005/0261375 A1 | 11/2005 | Ueno | |
| 2006/0122411 A1 | 6/2006 | Ueno et al. | |
| 2006/0240106 A1 | 10/2006 | Ueno | |

FOREIGN PATENT DOCUMENTS

WO   WO 2004/060377 A1   7/2004

OTHER PUBLICATIONS

The Merck Index, 17$^{th}$ edition (1999) pp. 221-223.*
Drossman et al., American Journal of Gastroenterology, 95(4) (2000), pp. 999-1007.*
http://www.askapatient.com/viewrating.asp?drug=20698&name=MIRALAX.*
Kinservik et al., "The efficacy and safety of polyethylene glycol 3350 in the treatment of constipation in children", Pediatric Nursing, May-Jun. 2004, vol. 30(3), pp. 232-237.*
"About Cystic Fibrosis", Cystic Fibrosis Foundation, downloaded on May 21, 2009 from "http://www.cff.org/AboutCF/", p. 1 of 1.*
Eggermont et al., "Small-intestinal abnormalities in cystic fibrosis patients", 1991, European Journal of Pediatrics, vol. 150, pp. 824-828.*
Chung et al., Canadian Family Physician, May 2009, vol. 55, pp. 481-482.*
http://www.askapatient.com/viewrating.asp?drug=20698&name=MIRALAX; downloaded on Mar. 11, 2008.*
L A Sorbera et al., "Lubiprostone. Treatment of Constipation, Treatment of Irritable Bowel Syndrome, Treatment of Postoperative Ileus, CIC-2 Channel Activator", Drugs of the Future, Apr. 2004, vol. 29, No. 4, pp. 336-341, XP008055565.
N J Talley, "Definitions, Epidemiology, and Impact of Chronic Constipation", Reviews in Gastroenterological Disorders, vol. 4, No. Suppl. 2, 2004, pp. S3-S10, XP0080055601.
Irvine E J et al.; Health-Related Quality of Life in Functional GI Disorders: Focus on Constipation and Resource Utilization; American Journal of Gastroenterology, vol. 97, No. 8, Aug. 2002, pp. 1986-1993.
Joseph H. Sellin, Intestinal Electrolyte Absorption and Secretion; Pathophysiology, Diagnosis, and Management, pp. 1451-1471 (WB Saunders Company, 1998), Chapter 86.
André Robert, Prostaglandins and the Gastrointestinal Tract, Chapter 57, Physiology of the Gastrointestinal Tract, edited by Leonard R. Johnson, Raven Press, New York, 1981, pp. 1407-1434.
D.S. Rampton, Prostanoids and intestinal physiology, Biology and Chemistry of Prostaglandins and Related Eicosanoids, pp. 323-344 (Churchill Livingstone, 1988).
C. J. Hawkey and D.S. Rampton; Prostaglandins and the Gastrointestinal Mucosa: Are They Important in Its Function, Disease, or Treatment?, Gastroenterology 1985; 89: 1162-88.
Charles E. Eberhart and Raymond N. Dubois; Eicosanoids and the Gastrointestinal Tract, Gastroenterology 1995; 109:285-301.
André Robert, Antisecretory, Antiulcer, Cytoprotective and Diarrheogenic Properties of Prostaglandins; Advances in Prostaglandin and Thromboxane Research, vol. 2, 1976, pp. 507-520.

(Continued)

*Primary Examiner* — Savitha Rao
*Assistant Examiner* — Gregg Polansky
(74) *Attorney, Agent, or Firm* — Sughrue Mion, PLLC

(57) ABSTRACT

The present invention relates to a method for the long term treatment of gastrointestinal disorders in a human subject, which comprises administering an effective amount of a halogenated prostaglandin compound and/or its tautomer to the subject. The method induces substantially no electrolyte shifting during the term of the treatment. The compound used in the present invention can improve quality of life in the human subjects with gastrointestinal disorders, are similarly effective in treating male and female subjects, and also effective in a human subject aged even 65 years and older.

17 Claims, 7 Drawing Sheets

(56) References Cited

OTHER PUBLICATIONS

I. H. M. Main, Pharmacology of prostaglandins, Postgraduate Medical Journal (1988) 64 (Suppl. 1), 3-6.

Sanders, Kenton M., Role of prostaglandins in regulating gastric motility; American Journal of Physiology, 247: G117-G126, American Physiological Society, 1984.

M. Pairet, T. Bouyssou, and Y. Ruckebusch, Colonic formation for soft feces in rabbits: a role for endogenous prostaglandins; American Journal of Physiology, 250: G302-G308, American Physiological Society, 1986.

Timothy S. Gaginella, Eicosanoid-Mediated Intestinal Secretion; Textbook of Secretory Diarrhea, Raven Press, New York, 1990, pp. 15-30.

Jon P. Monk and Stephen P. Clissold, Misoprostol: A Preliminary Review of Its Pharmacodynamic and Pharmacokinetic Properties, and Therapeutic Efficacy in the Treatment of Peptic Ulcer Disease; Drugs 33: 1-30 (1987) ADIS Press Limited.

Nathaniel F. Pierce, M.D., Charles C.J. Carpenter, Jr., M.D., Herbert L. Elliott, M.D., and William B. Greenough, III, M.D., Effects of Prostaglandins, Theophylline, and Cholera Exotoxin upon Transmucosal Water and Electrolyte Movement in the Canine Jejunum; Gastroenterology, vol. 60, No. 1, 1971, pp. 22-32.

Eckhard Beubler, Klaus Bukhave, and Jørgen Rask-Madsen, Significance of Calcium for the Prostaglandin $E_2$—Mediated Secretory Response to 5-Hydroxytryptamine in the Small Intestine of the Rat In Vivo; Gastroenterology 1986; 90: 1972-7.

L.L. Clarke and R.A. Argenzio, NaCl transport across equine proximal colon and the effect of endogenous prostanoids; American Journal of Physiology, 259: G62-G69, American Physiological Society, 1990.

J.M. Hunt & E.L. Gerring, The effect of prostaglandin $E_1$ on motility of the equine gut; J. Vet. Pharmacol. Therap. 8, 165-173, 1985.

J.L. Wallace & A.W. Tigley, Review article: new insights into prostaglandins and mucosal defence; Aliment Pharmacol Ther 1995; 9: 227-235.

MIRALAX™, Polyethylene Glycol 3350, NF Powder for Solution Package insert, Braintree Laboratories, Inc., TRE-0571, Nov. 2001.

ZELNORM® (tegaserod maleate) Package insert, Novartis, T2004-53/T2004-54, 89015305, (2004).

A. Robert, J.E. Nezamis, C. Lancaster, A.J. Hanchar, and M.S. Klepper, Enteropooling Assay: A Test for Diarrhea Produced by Prostaglandins; Prostaglandins, May 1976, vol. II, No. 5, 809-828.

Esam Z. Dajani, Erik A.W. Roge and Ralph E. Bertermann; Effects of E Prostaglandins, Diphenoxylate and Morphine on Intestinal Motility In Vivo, European Journal of Pharmacology, 34 (1975) 105-113.

* cited by examiner

Group A: 18≤Age<50, Group B: 50≤Age<65, Group C: 65≤Age

METHOD FOR TREATING GASTROINTESTINAL DISORDER

CROSS REFERENCE TO RELATED APPLICATIONS

This application claims benefit from U.S. Provisional Application No. 60/606,521 filed on Sep. 2, 2004, U.S. Provisional Application No. 60/666,317 filed on Mar. 30, 2005, and U.S. Provisional Application No. 60/666,593 filed on Mar. 31, 2005 in the United States Patent and Trademark Office, the disclosures of which are incorporated herein in their entirety by reference.

TECHNICAL FIELD

The present invention relates to a method and composition for the long-term treatment of gastrointestinal disorders in a human subject.

The present invention also relates to a method and composition for the treatment of gastrointestinal disorders in both male and female human subject.

The present invention further relates to a method and composition for the treatment of gastrointestinal disorders in a human subject aged 65 years and older.

Furthermore, the present invention relates to a method and composition for the improvement of quality of life in a human subject with gastrointestinal disorders.

BACKGROUND ART

Constipation is generally defined as infrequent and difficult passage of stool. Medical reporting estimates that one of every 50 people in the United States suffers from constipation. That is, one of the most common disorders among Americans. Constipation is more likely to affect females than males and more likely to occur in older adults, showing an exponential increase after the age of 65. The actual occurrence of constipation is likely higher than reported, as many individuals suffer at home without seeking professional care.

Although in some instances constipation may be caused by obstruction, most constipation can be associated with factors such as a diet low in soluble and insoluble fibers, inadequate exercise, medication use (in particular, opiate analgesics, anticholinergic antidepressants, antihistamines, and vinca alkaloids), bowel disorders, neuromuscular disorders, metabolic disorders, poor abdominal pressure or muscular atony.

A precise quantitative definition of constipation has been difficult to establish due to the wide range of perceived "normal" bowel habits, as well as the diverse array of symptoms and signs associated with constipation. The FDA has recognized a need for prescriptive treatment of occasional constipation.

Prostaglandins (hereinafter, referred to as PGs) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

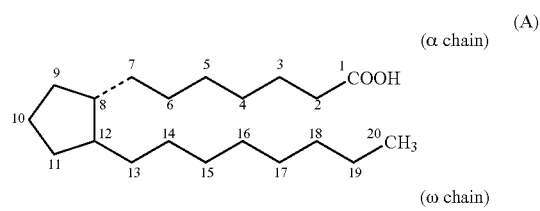 [SMILES: "(a chain)" ; CCCCCCCCC1CCC[C@@H]1CCCCCCC(=O)O ; "(w chain)"]

PGs are classified into several types according to the structure and substituents on the five-membered ring, for example, Prostaglandins of the A series (PGAs);

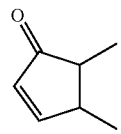

Prostaglandins of the B series (PGBs);

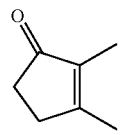

Prostaglandins of the C series (PGCs);

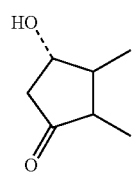

Prostaglandins of the D series (PGDs);

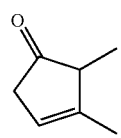

Prostaglandins of the E series (PGEs);

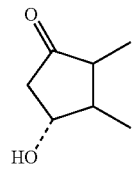

Prostaglandins of the F series (PGFs);

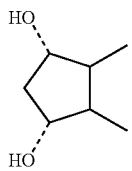

and the like. Further, they are classified into PG$_1$s containing a 13,14-double bond; PG$_2$s containing, 5,6- and 13,14-double bonds; and PG$_3$s containing 5,6-, 13,14- and 17,18-double bonds. PGs are known to have various pharmacological and physiological activities, for example, vasodilatation, inducing of inflammation, platelet aggregation, stimulating uterine muscle, stimulating intestinal muscle, anti-ulcer effect and the like. The major prostaglandins produced in the human gastrointestinal (GI) system are those of the E, I and F series (Sellin, Gastrointestinal and Liver Disease: Pathophysiology, Diagnosis, and Management. (WB Saunders Company, 1998); Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., Gastroenterology, 109: 285-301 (1995)).

Under normal physiological conditions, endogenously produced prostaglandins play a major role in maintaining GI function, including regulation of intestinal motility and transit, and regulation of fecal consistency. (Sellin, Gastrointestinal and Liver Disease: Pathophysiology, Diagnosis, and Management. (WB Saunders Company, 1998); Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., *Gastroenterology*, 109: 285-301 (1995); Robert, *Adv Prostaglandin Thromboxane Res*, 2:507-520 (1976); Main, et al., *Postgrad Med J*, 64 Suppl 1: 3-6 (1988); Sanders, *Am J Physiol*, 247: G117 (1984); Pairet, et al., *Am J Physiol.*, 250 (3 pt 1): G302-G308 (1986); Gaginella, Textbook of Secretory Diarrhea 15-30 (Raven Press, 1990)). When administered in pharmacological doses, both PGE$_2$ and PGF$_{2\alpha}$ have been shown to stimulate intestinal transit and to cause diarrhea (Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Robert, *Adv Prostaglandin Thromboxane Res*, 2:507-520 (1976)). Furthermore, the most commonly reported side effect of misoprostol, a PGE$_1$ analogue developed for the treatment of peptic ulcer disease, is diarrhea (Monk, et al., Drugs 33 (1): 1-30 (1997))

PGE or PGF can stimulate the intestines and cause intestinal contraction, but the enteropooling effect is poor. Accordingly, it is impossible to use PGEs or PGFs as cathartics because of side effects such as stomachache caused by the intestinal contraction.

Multiple mechanisms, including modifying enteric nerve responses, altering smooth muscle contraction, stimulating mucous secretion, stimulating cellular ionic (in particular electrogenic Cl⁻ transport) and increasing intestinal fluid volume have been reported to contribute to the GI effects of prostaglandins (Robert, Physiology of the Gastrointestinal Tract 1407-1434 (Raven, 1981); Rampton, Prostaglandins: Biology and Chemistry of Prostaglandins and Related Eicosanoids 323-344 (Churchill Livingstone, 1988); Hawkey, et al., *Gastroenterology*, 89: 1162-1188 (1985); Eberhart, et al., Gastroenterology, 109: 285-301 (1995); Robert, *Adv Prostaglandin Thromboxane Res*, 2:507-520 (1976); Main, et al., Postgrad Med J, 64 Suppl 1: 3-6 (1988); Sanders, *Am J Physiol*, 247: G117 (1984); Pairet, et al., *Am J Physiol*, 250 (3 pt 1): G302-G308 (1986); Gaginella, Textbook of Secretory Diarrhea 15-30 (Raven Press, 1990); Federal Register Vol. 50, No. 10 (GPO,1985); Pierce, et al., *Gastroenterology* 60 (1): 22-32 (1971); Beubler, et al., *Gastroenterology*, 90: 1972 (1986); Clarke, et al., *Am J Physiol* 259: G62 (1990); Hunt, et al., *J Vet Pharmacol Ther*, 8 (2): 165-173 (1985); Dajani, et al., *Eur J Pharmacol*, 34(1): 105-113 (1975); Sellin, Gastrointestinal and Liver Disease: Pathophysiology, Diagnosis, and Management 1451-1471 (WB Saunders Company, 1998)). Prostaglandins have additionally been shown to have cytoprotective effects (Sellin, Gastrointestinal and Liver Disease: Pathophysiology, Diagnosis, and Management. (WB Saunders Company, 1998); Robert, *Physiology of the Gastrointestinal Tract* 1407-1434 (Raven, 1981); Robert, *Adv Prostaglandin Thromboxane Res* 2:507-520 (1976); Wallace, et al., Aiiment Pharmacol Ther 9: 227-235 (1995)).

U.S. Pat. No. 5,317,032 to Ueno et al. describes prostaglandin analog cathartics, including the existence of bicyclic tautomers of the same and U.S. Pat. No. 6,414,016 to Ueno describes bicyclic tautomers of a prostaglandin analog as having pronounced activity as anti-constipation agents. The bicyclic tautomers of a prostaglandin analog, which is substituted at the C-16 position by one or more halogen atoms, especially fluorine atoms, can be employed in small doses for relieving constipation.

U.S. Patent publication No. 2003/0130352 to Ueno et al. describes that prostaglandin compound opens and activates chloride channels, especially ClC channels, more especially ClC-2 channel.

U.S. Patent publication No. 2003/0119898 to Ueno et al. describes specific composition of a halogenated prostaglandin analog for the treatment and prevention of constipation.

U.S. Patent publication No. 2004/0138308 to Ueno et al. describes that a chloride channel opener, especially a prostaglandin compound can be used for the treatment of abdominal discomfort, and for the treatment of functional gastrointestinal disorders such as irritable bowel syndrome and functional dyspepsia.

MiraLax™ (polyethylene Glycol 3350, NF Powder for solution) is synthetic polyglycol having an average molecular weight of 3350, and used for the treatment of occasional constipation. This product is basically used for up to two weeks. Prolonged, frequent or excessive use of MiraLax™ may result in electrolyte imbalance and dependence on laxatives (MiraLax™ Package insert). MiraLax™ acts as an osmotic agent, which creates an imbalance in the lumen of the gut and draws fluid osmotically into the lumen. The increased fluid level softens the stool and promotes bowel movements.

Likewise, the aforesaid ClC-2 chloride channel activators are believed to function by stimulating chloride secretion into the lumen of the gut, which draws water through an osmotic mechanism into the lumen that, in turn, promotes bowel movements. Given that a specific prostaglandin compound is an ion channel activator and is believed to work essentially in an osmotic manner, like Miralax™, one would expect that long term use of said prostaglandin compound would also have the disadvantages found in MiraLax™. Therefore, its use would be limited practically to a couple of weeks, just like Miralax™.

Zelnorm® (tegaserod maleate) is indicated for the short-term treatment of women with irritable bowel syndrome (IBS), whose primary bowel symptom is constipation. In two randomized, placebo-controlled, double-blind studies enrolling 288 males, there were no significant differences between placebo and Zelnorm® response rates. The safety and effectiveness of Zelnorm® in men with IBS with constipation has not been established. In addition, Subgroup analyses of patients aged 65 years and older showed no significant treatment effect for Zelnorm® over placebo. That is, the effectiveness of Zelnorm® in patients aged 65 years and older with chronic idiopathic constipation has not been established. Further, if the patients stop taking Zelnorm®, the symptoms may return within 1 or 2 weeks. (Zelnorm® Package insert)

SUMMARY OF THE INVENTION

Despite the essentially osmotic mechanism of action, however, the inventor has found surprisingly that there is no electrolyte shifting on using certain halogenated prostaglandin compounds in human patients during long term use.

The inventor has also found that halogenated prostaglandin compounds are effective in a long-term treatment and that substantially no rebound effect is seen after the discontinuation of even the long-term treatment with said compound.

Furthermore, the inventor has found that halogenated prostaglandin compounds improve the quality of life in the patients with gastrointestinal disorders and are similarly effective in treating male and female human patients, and even 65 years and older patients.

Namely, the present invention provides a method for the long term treatment of gastrointestinal disorders in a human subject, which comprises administering an effective amount of a prostaglandin compound represented by Formula (I) and/or its tautomer:

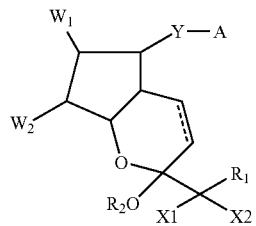

wherein $W_1$ and $W_2$ are

$R_3$ and $R_4$ are hydrogen; or one of them is OH and the other is hydrogen;

$X_1$ and $X_2$ are hydrogen, lower alkyl or halogen, provided that at least one of them is halogen;

$R_2$ is hydrogen or alkyl;

Y is a saturated or unsaturated $C_{2-10}$ hydrocarbon chain, which is unsubstituted or substituted by oxo, halogen, alkyl, hydroxy or aryl;

A is —$CH_2OH$, —$COCH_2OH$, —COOH or its functional derivative;

$R_1$ is a saturated or unsaturated, straight chain-, branched chain- or ring-forming lower hydrocarbon, which is unsubstituted or substituted by halogen, oxo, hydroxy, lower alkyl, lower alkoxy, lower alkanoyloxy, lower cycloalkyl, lower cycloalkyloxy, aryl, or aryloxy; lower cycloalkyl; lower cycloalkyloxy; aryl; or aryloxy;

the bond between C-13 and C-14 positions is double or single bond, and the steric configuration at C-15 position is R, S or a mixture thereof to the subject in need thereof.

The present invention also provides a method for the treatment of gastrointestinal disorders in a male human subject, or a human subject aged 65 years and older, which comprises administering an effective amount of a prostaglandin compound represented by Formula (I) and/or its tautomer to the subject in need thereof.

The present invention further provides a method for the improvement of quality of life in a human subject with gastrointestinal disorders, which comprises administering an effective amount of a prostaglandin compound represented by Formula (I) and/or its tautomer to the subject in need thereof.

In each embodiment of the method of the present invention, total daily dose of the PG compound may preferably be 6-96 μg.

The method of the present invention can be carried out by administering a pharmaceutical composition which comprises the above-identified prostaglandin compound and/or its tautomer to the subject to be treated. Accordingly, in another aspect of the present invention, a pharmaceutical composition for the long term treatment of gastrointestinal disorders in a human subject comprising (i) an effective amount of a prostaglandin compound represented by Formula (I) and/or its tautomer and (ii) a pharmaceutically suitable excipient is provided.

The present invention further provides a

Pharmaceutical composition for the treatment of gastrointestinal disorder in both male and female patients or in a human subject aged 65 years and older, which comprises (i) an effective amount of a prostaglandin compound represented by Formula (I) and/or its tautomer and (ii) a pharmaceutically suitable excipient.

The present invention still further provides a pharmaceutical composition for the improvement of quality of life in a human subject with gastrointestinal disorders, which comprises (i) an effective amount of a prostaglandin compound represented by Formula (I) and/or its tautomer and (ii) a pharmaceutically suitable excipient.

In another aspect of the present invention, use of a prostaglandin compound represented by Formula (I) and/or its tautomer for the manufacture of a pharmaceutical composition as defined above is provided.

DETAILED DESCRIPTION OF THE INVENTION

Figure 1:
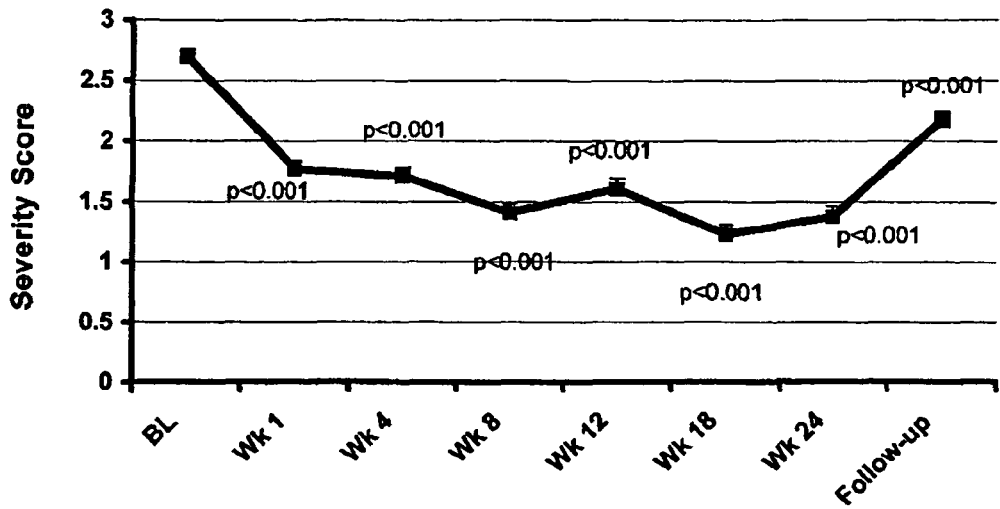
FIG. 1 is a graph showing severity of constipation during the treatment for 6 months.
Figure 2:
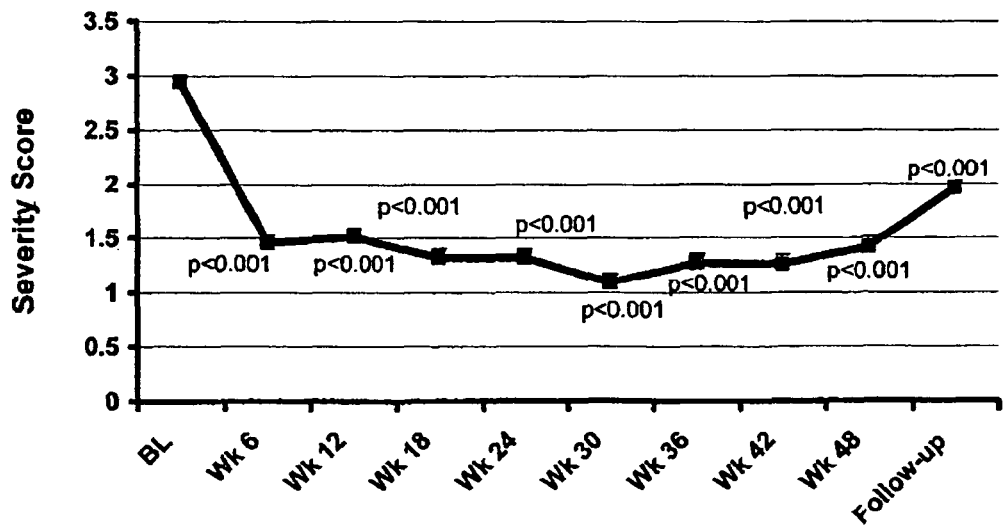
FIG. 2 is a graph showing severity of constipation during the treatment for 12 months.
Figure 3:
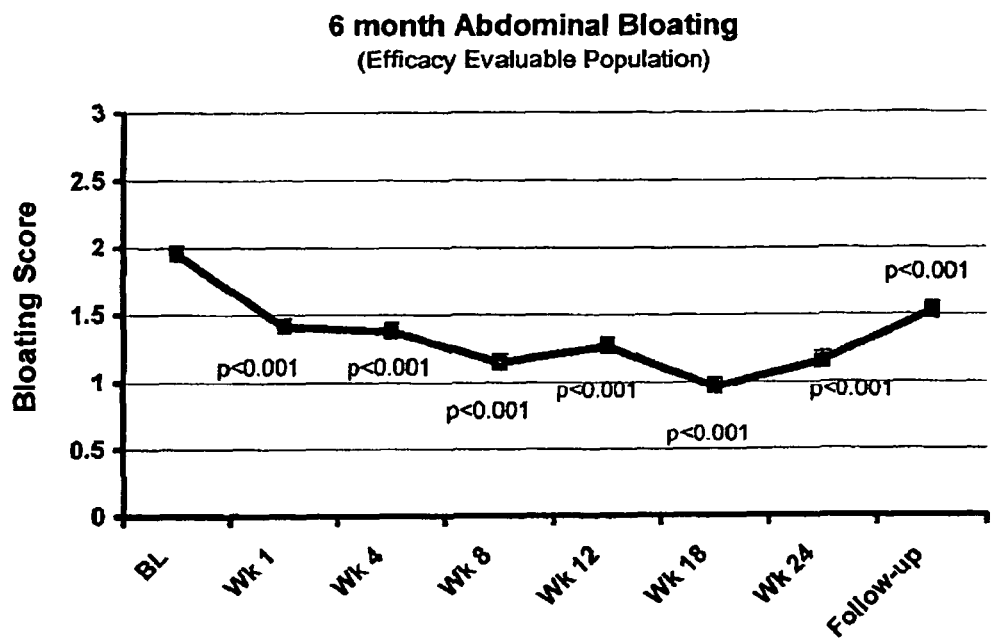
FIG. 3 is a graph showing abdominal bloating during the treatment for 6 months.
Figure 4:
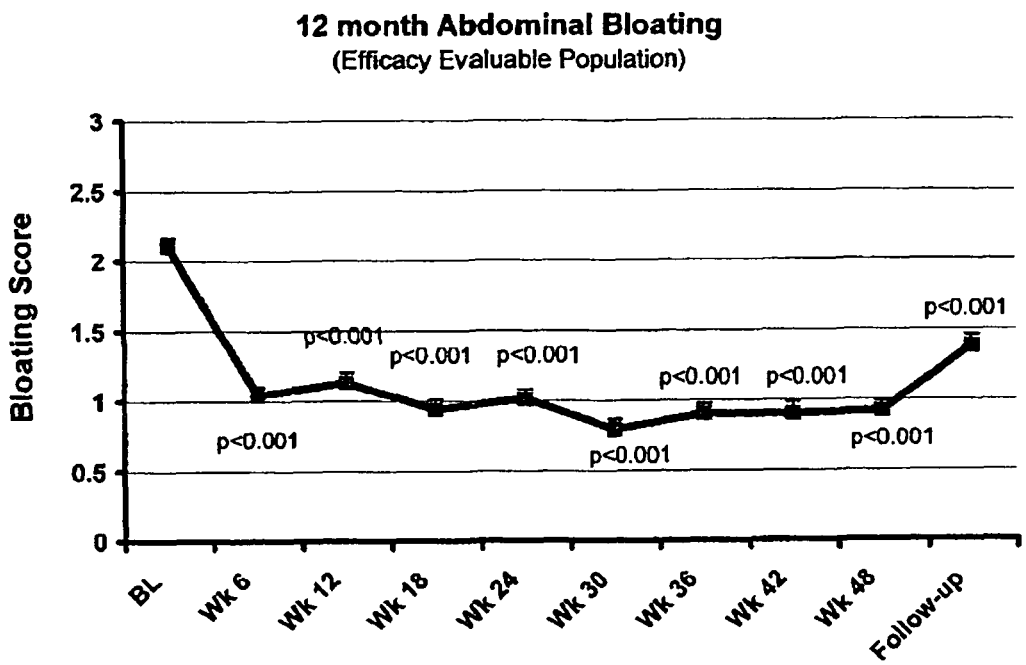
FIG. 4 is a graph showing abdominal bloating during the treatment for 12 months.
Figure 5:
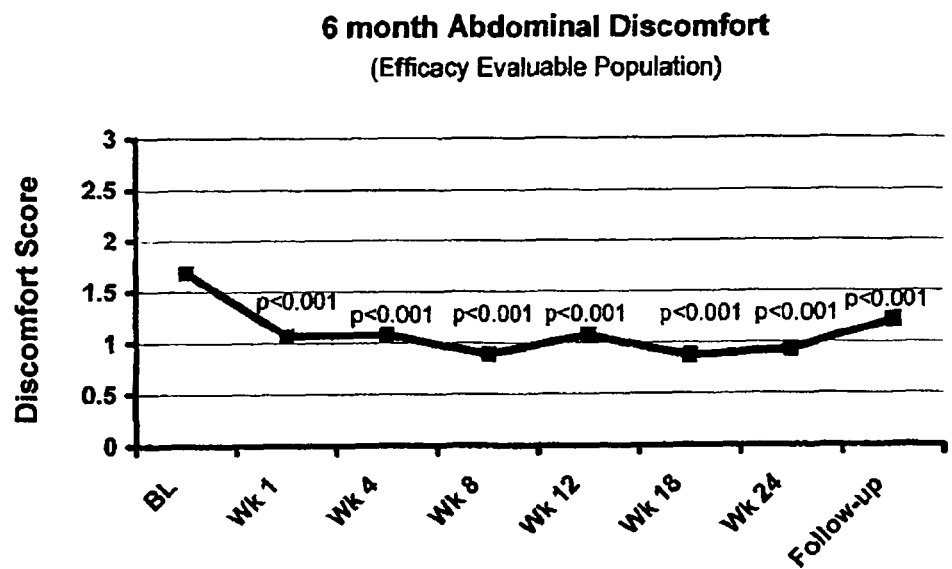
FIG. 5 is a graph showing abdominal discomfort during the treatment for 6 months.
Figure 6:
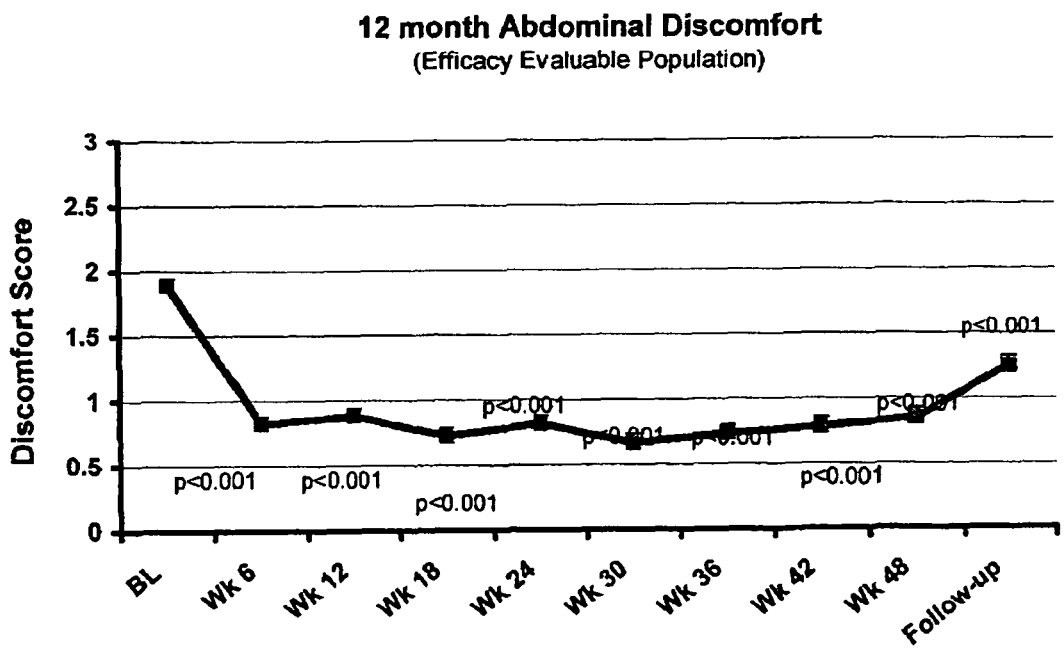
FIG. 6 is a graph showing abdominal discomfort during the treatment for 12 months.
Figure 7:
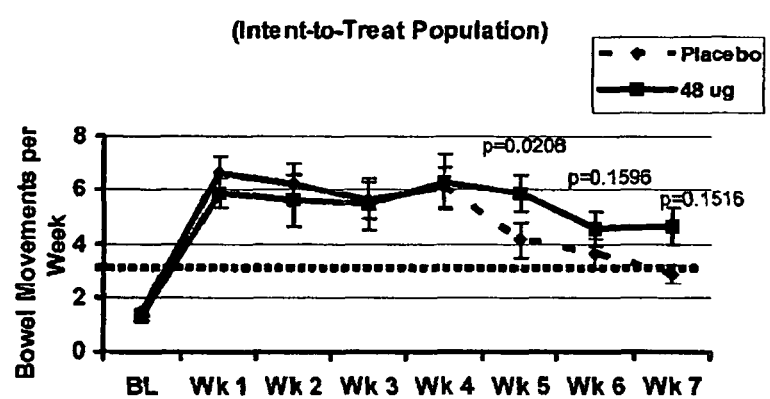
FIG. 7 is a graph showing effects on bowel movements per week.
Figure 8:
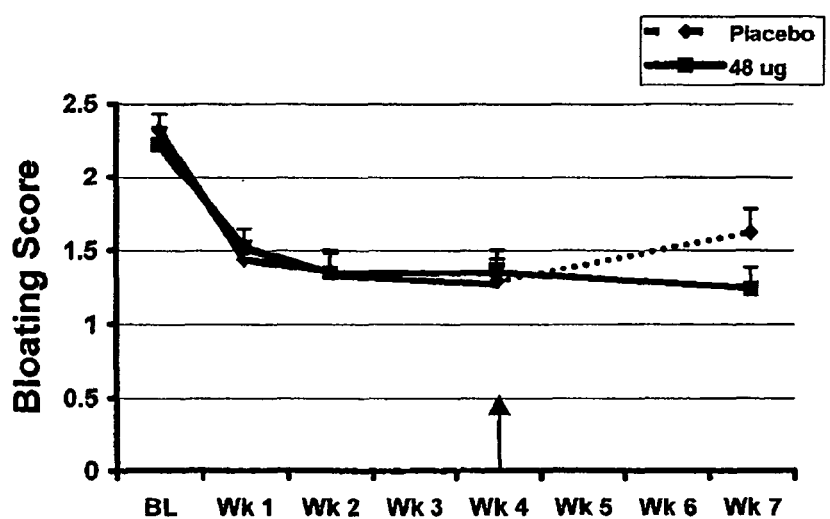
FIG. 8 is a graph showing effects on abdominal bloating.
Figure 9:
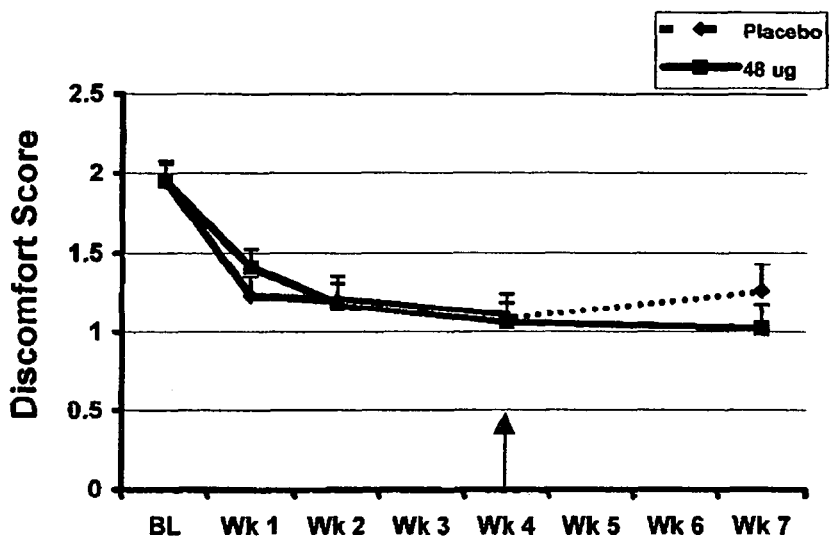
FIG. 9 is a graph showing effects on abdominal discomfort.
Figure 10:
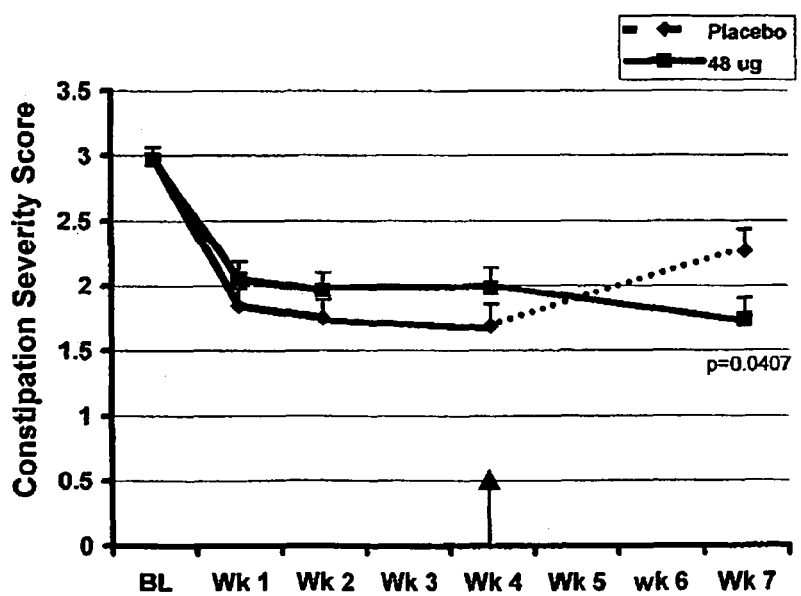
FIG. 10 is a graph showing effects on severity of Constipation.
Figure 11:
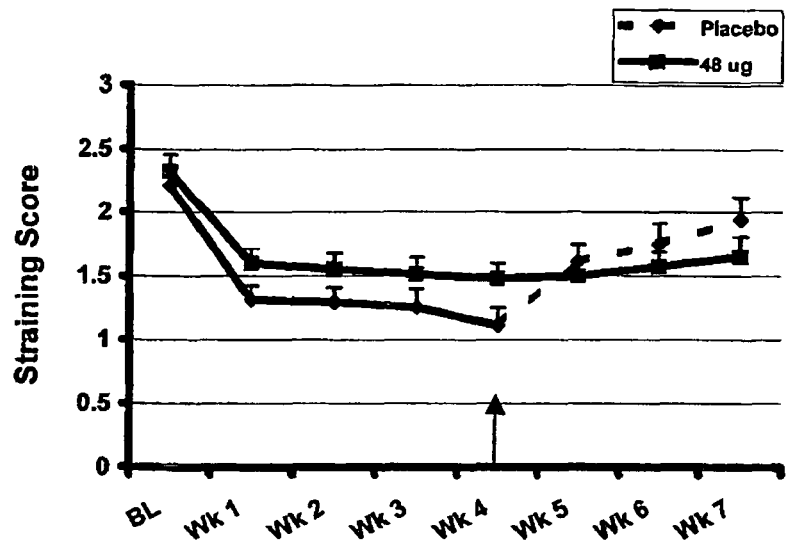
FIG. 11 is a graph showing effects on straining.
Figure 12:
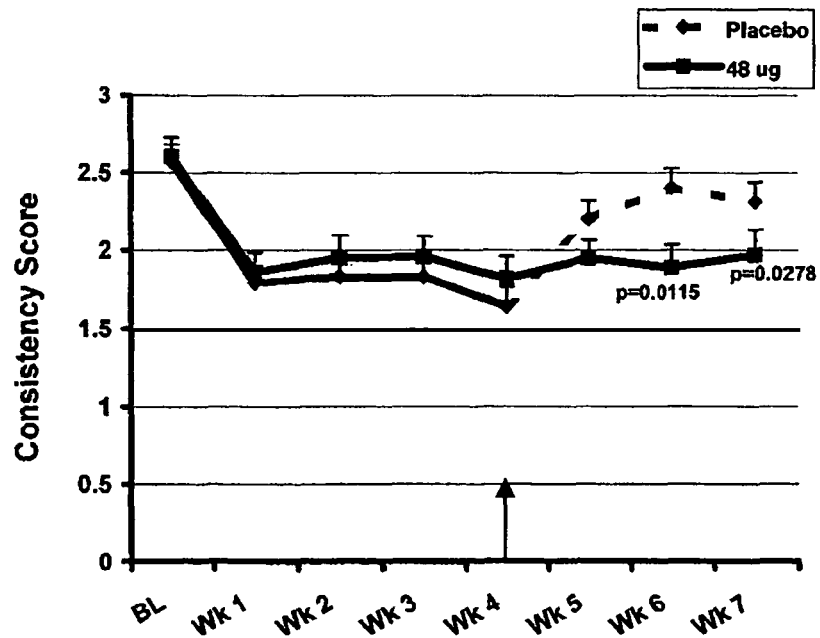
FIG. 12 is a graph showing effects on Consistency.

In the present invention, the "effective amount" may be determined based on the age, body weight, conditions of the patient to be treated, desired therapeutic effect, administration route, treatment period and the like. According to the present invention, the amount of the prostaglandin compound to be administered may be 0.001-1000 µg/kg body weight, more preferably, 0.01-100 µg/kg body weight and most preferably, 0.1-10 µg/kg body weight per day. The frequency of administration may be one or more times per day, preferably, two or more times per day. Typical administration amount to a patient is about 6-96 µg per day. According to the specification and claims, the administration amount or dose is determined based on a patient having body weight of approximately 60 kg.

As used herein, the term "about" when used in conjunction with a unit of measure can be defined as +/−30%, preferably +/−20%, and especially +/−10%. For example, the total daily dose of about 6-96 µg preferably means the range of 5.4-105.6 µg. The preferred dose is in the range of about 6-72 µg. In a more preferred embodiment, the dose is in the range of about 6-60 µg. For example, the dose of said halogenated compound can be about 8-48 µg.

(i) Prostaglandin Compound of Formula (I)

The instant invention utilizes a prostaglandin compound represented by formula (I):

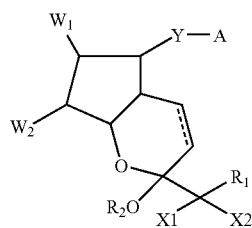

wherein $W_1$ and $W_2$ are

$R_3$ and $R_4$ are hydrogen; or one of them is OH and the other is hydrogen;

$X_1$ and $X_2$ are hydrogen, lower alkyl or halogen, provided that at least one of them is halogen;

$R_2$ is hydrogen or alkyl;

Y is a saturated or unsaturated $C_{2-10}$ hydrocarbon chain, which is unsubstituted or substituted by oxo, halogen, alkyl, hydroxy or aryl;

A is —$CH_2OH$, —$COCH_2OH$, —COOH or its functional derivative;

$R_1$ is a saturated or unsaturated, straight chain-, branched chain- or ring-forming lower hydrocarbon, which is unsubstituted or substituted by halogen, oxo, hydroxy, lower alkyl, lower alkoxy, lower alkanoyloxy, lower cycloalkyl, lower cycloalkyloxy, aryl, or aryloxy; lower cycloalkyl; lower cycloalkyloxy; aryl; or aryloxy;

the bond between C-13 and C-14 positions is double or single bond, and the steric configuration at C-15 position is R, S or a mixture thereof.

In the above formula, the term "halogen" is used to include fluorine, chlorine, bromine, and iodine atoms. Particularly preferable halogen atoms for $X_1$ and $X_2$ are fluorine atoms.

The term "unsaturated" in the definitions for $R_1$ and Y is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower" throughout the specification and claims is intended to include a group having 1 to 6 carbon atoms unless otherwise specified.

The term "ring" refers to lower cycloalkyl, lower cycloalkyloxy, aryl or aryloxy.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkoxy" refers to a group of lower alkyl-O—, wherein lower alkyl is as defined above.

The term "lower alkanoyloxy" refers to a group represented by the formula RCO—O—, wherein RCO— is an acyl group formed by oxidation of a lower alkyl group as defined above, such as acetyl.

The term "lower cycloalkyl" refers to a cyclic group formed by cyclization of a lower alkyl group as defined above but contains three or more carbon atoms, and includes, for example, cyclopropyl, cyclobutyl, cyclopentyl and cyclohexyl.

The term "lower cycloalkyloxy" refers to the group of lower cycloalkyl-O—, wherein lower cycloalkyl is as defined above.

The term "aryl" refers to unsubstituted or substituted aromatic carbocyclic or heterocyclic groups (preferably monocyclic groups), for example, phenyl, naphthyl, tolyl, xylyl, furyl, thienyl, pyrrolyl, oxazolyl, isoxazolyl, thiazolyl, isothiazolyl, imidazolyl, pyrazolyl, furzanyl, pyranyl, pyridyl, pyridazyl, pyrimidryl, pyrazyl, pyrrolidinyl, imidazolidinyl, pyrazolidinyl, piperidino, piperazinyl, morpholono, indolyl, benzothienyl, quinolyl, isoquinolyl, puryl, quinazolinyl, carbazolyl, acridinyl, phenathridinyl, benzimidazolyl, benzimidazolonyl, benzothiazolyl and phenothiazinyl. Examples of substituents are halogen atom and halo (lower)alkyl, wherein halogen atom and lower alkyl are as defined above.

The term "aryloxy" refers to a group represented by the formula ArO—, wherein Ar is aryl as defined above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A means a group represented by the formula —CONR'R", wherein each of R' and R" is hydrogen, lower alkyl, aryl, alkyl- or aryl-sulfonyl, lower alkenyl and lower alkynyl, and includes for example, lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Examples of Y include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH ($CH_3$)—$CH_2$—,
—$CH_2$—$CH_2$—$CH_2$—$CH_2$—CH ($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH ($CH_3$)—$CH_2$—.

Further, at least one carbon atom in the aliphatic hydrocarbon of Y is optionally substituted by oxygen, nitrogen or sulfur.

Preferred A is —COOH or its pharmaceutically acceptable salt or ester.

Preferred $X_1$ and $X_2$ are both being halogen atoms, and more preferably, fluorine atoms.

Preferred $W_1$ is =O.

Preferred $W_2$ is

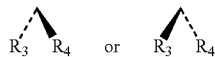

where $R_3$ and $R_4$ are both hydrogen atoms.

Preferred Y is an unsubstituted, saturated or unsaturated hydrocarbon chain having 6-8 carbon atoms.

Preferred $R_1$ is a hydrocarbon containing 1-6 carbon atoms, more preferably, 1-4 carbon atoms. $R_1$ may have one or two side chains having one carbon atom.

$R_2$ is preferably hydrogen.

Most preferred embodiment is a prostaglandin compound of formula (I) in which A is —COOH; Y is $(CH_2)_6$; $W_1$ is =O; $W_2$ is

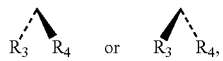

wherein $R_3$ and $R_4$ are both hydrogen; $R_2$ is hydrogen; $X_1$ and $X_2$ are fluorine; and $R_1$ is $(CH_2)_3CH_3$ or $CH_2CH(CH_3)$ $CH_2CH_3$.

The active agent of this invention or the PG compound of formula (I) exists as a bicyclic compound in a solid state, but when dissolved in a solvent, a part of the compound forms a tautomer. In the absence of water, compound represented by formula (I) exists predominantly in the form of the bicyclic structure. In aqueous media, it is believed that hydrogen bonding occurs between the water molecule and, for example, the keto moiety at the C-15 position, thereby hindering bicyclic ring formation. In addition, it is believed that the halogen atoms at the C-16 position promote bicyclic ring formation. The tautomerism between the hydroxy at the C-11 position and the keto moiety at the C-15 position, shown below, is especially significant in the case of compounds having a 13,14 single bond and two fluorine atoms at the C-16 position.

Accordingly, the present invention may comprise isomers of the halogenated prostaglandin compounds. For example, mono-cyclic tautomers having a keto group at the C-15 position and halogen atoms at the C-16 position is shown as follows.

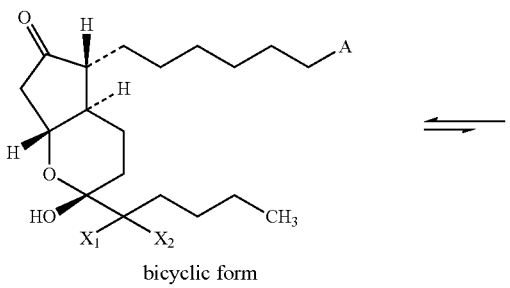

bicyclic form

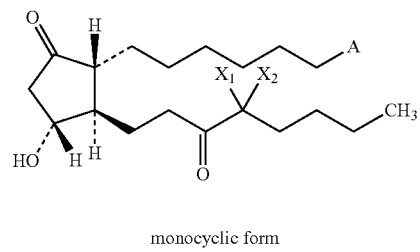

monocyclic form

A preferred compound according to the invention in its monocyclic form can be named as 13,14-dihydro-15-keto-16,16-difluoro-PGE$_1$, according to conventional prostaglandin nomenclature.

(ii) The Pharmaceutically Suitable Excipient

According to the invention, the pharmaceutical composition may be formulated in any form. The pharmaceutically suitable excipient may be, therefore, selected depending on the desired form of the composition. According to the invention, "pharmaceutically suitable excipient" means an inert substance, which is combined with the active ingredient of the invention and suitable for preparing the desired form.

For example, a solid composition for oral administration of the present invention may include tablets, preparations, granules and the like. In such a solid composition, one or more active ingredients may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the usual work-up, the composition may contain additives other than inactive diluent, for example, lubricant such as magnesium stearate; disintegrant such as fibrous calcium gluconate; stabilizer such as cyclodextrin, for example, α,β- or γ-cyclodextrin; etherified cyclodextrin such as dimethyl-α-, dimethyl-β-, trimethyl-β-, or hydroxypropyl-β-cyclodextrin; branched cyclodextrin such as glucosyl-, maltosyl-cyclodextrin; formylated cyclodextrin, cyclodextrin containing sulfur; phospholipid and the like. When the above cyclodextrins are used, inclusion compound with cyclodextrins may be sometimes formed to enhance stability. Alternatively, phospholipid may be sometimes used to form liposome, resulting in enhanced stability.

Tablets or pills may be coated with film soluble in the stomach or intestine such as sugar, gelatin, hydroxypropyl cellulose, hydroxypropylmethyl cellulose phthalate as needed. Further, they may be formed as capsules with absorbable substances such as gelatins. Preferably, the composition is formulated in a soft gelatin capsule with liquid contents of the halogenated prostaglandin compound and a medium chain fatty acid triglyceride. Examples of the medium chain fatty acid triglyceride used in the present invention include a triglyceride of a saturated or unsaturated fatty acid having 6-14 carbon atoms which may have a branched chain. A preferred fatty acid is a straight chain saturated fatty acid, for example caproic acid (C6), caprylic acid (C8), capric acid (C10), lauric acid (C12) and myristic acid (C14). In addition, two or more medium chain fatty acid triglycerides may be used in combination. Further suitable excipients are disclosed in the published PCT application WO 01/27099.

A liquid composition for oral administration may be in the form of emulsion, solution, suspension, syrup or elixir comprising a generally used inactive diluent. Such composition may contain, in addition to the inactive diluent, additives such as lubricants, sweetening agents, flavoring agents, preservatives, solubilizers, anti-oxidants and the like. The additives may be selected from those described in any general textbooks in the pharmaceutical field. Such liquid compositions may be directly enclosed in soft capsules. The composition of the present invention may be suppository, enema or the like. They may be in the form of, for example, sterile aqueous or non-aqueous solution, suspension, emulsion, and the like. Examples of the excipients for the aqueous solution, suspension or emulsion may include, for example, distilled water, physiological saline and Ringer's solution.

Examples of excipients for non-aqueous solution, suspension or emulsion may include, for example, propylene glycol, polyethylene glycol, fatty acid triglyceride, vegetable oil such as olive oil, alcohols such as ethanol, polysorbate and the like. Such composition may contain additives such as preservatives, wetting agent, emulsifier, dispersant, anti-oxidants and the like.

According to the present invention, the pharmaceutical composition may be either for parenteral or oral administration and an orally applicable composition is preferred. In an example, the active ingredient is preferably dissolved medium chain fatty acid triglyceride and filled in a capsule.

According to the method of the invention, the composition of the present invention can be administered systemically or locally by means of oral or parenteral administration, including parenteral administration using suppository, enema and the like. The composition of the present invention may be administered once to several times per day.

Preferably, the total daily dose of the prostaglandin compound of the present invention is in the range of about 6-96 μg, more preferably about 6-72 μg, still more preferably about 6-60 μg and especially, 8-48 μg. The dose may vary somewhat, at the discretion of the physician, depending the age and body weight of the patient, conditions, therapeutic effect, administration route, treatment period and the like.

The term "substantially no electrolyte shifting" used herein means that electrolyte imbalance during the term of the treatment is far less than that induced by a known electrolyte imbalance inducing agent. Moreover, the term "substantially no electrolyte shifting" refers to serum electrolyte levels in a treated patient that are within clinically normal ranges as they would be understood by the clinician. As described above, MiraLax™, that is used for the treatment of constipation may induce electrolyte imbalance, which can result in, among other things, dangerous cardiac problems. On the other hand, as shown in the following example, the prostaglandin compound used in the instant invention induces substantially no electrolyte shifting even if it is administered for long term.

The following examples also show that the pharmaceutical composition of the present invention induces substantially no rebound constipation or the other disadvantage after stopping the prolonged treatment with the composition. Accordingly, it can be resulted in that the composition of the present invention is useful for long term treatment.

Furthermore, the assessment of quality of life in both constipation and IBS patients observed that the present compounds improved the quality of life in the patients.

According to the present invention, the present compounds are useful for the long-term treatment of gastrointestinal disorders. It is similarly effective in treating male and female patients. In addition it is useful in treating a patient aged 65 years and older.

The "gastrointestinal disorders" used herein include for example, but not limited to, acute or chronic constipation, functional gastrointestinal disorders such as irritable bowel syndrome and functional dyspepsia, gastric ulcer, large or small intestinal ulcer and abdominal discomfort.

Included in the types of constipation to be treated, although not particularly limited, are functional constipation such as relaxing constipation, spastic constipation, rectal constipation and post operative ileus; organic constipation caused by intestinal diseases and stenosis due to postoperative adhesion; and constipation induced by a drug such as opioid.

In addition to relieving or preventing constipation, the present composition may be used for preventing a patient with hernia or cardiovascular diseases from straining at stool, or for softening feces of a patient with anorectal diseases. Moreover, the present composition may be used for cleansing the gastrointestinal tract in preparation for endoscopic examination or for diagnostic or surgical procedures such as colonoscopy, barium enema X-rays and intravenous pyelography, and emergency procedures such as emergency gastrointestinal flush for poison removal and the like. Accordingly the invention covers embodiments wherein the composition of the present invention is used for cleansing the gastrointestinal tract in a human male subject or a human subject aged 65 years and older in need thereof.

The term "treatment" used herein includes any means of control such as prevention, care, relief of symptoms, attenuation of symptoms and arrest of progression. The term "long term treatment" used herein means administering the compound for at least two weeks. The compound may be administered everyday for the whole term of the treatment or with an interval of one to several days. In a particular embodiment of the present invention, the prostaglandin compound is administered for at least three weeks. In another particular embodiment, the prostaglandin compound is administered for at least four weeks. In another particular embodiment, the prostaglandin compound is administered for at least 2 months. In another particular embodiment, the prostaglandin compound is administered for at least 6 months.

The further details of the present invention will follow with reference to test examples, which, however, are not intended to limit the present invention.

Example 1

(Method)

Multi-center, open-label study was performed to evaluate the safety of 48 μg of Compound A (13,14-dihydro-15-keto-16,16-difluoro-$PGE_1$) (24 μg of Compound A b.i.d) when administered daily for 24 weeks (6 months) or 48 weeks (12 months) to subjects with occasional constipation. Patients who demonstrated history of chronic constipation for at least 3 months (having less then three SBMs per week) and at least one associated symptom such as hard stools, incomplete evacuation, straining were enrolled. After 14-day drug-free washout period, they received 48 μg of Compound A (24 μg of Compound A b.i.d) orally for 48 weeks.

In this study, the following parameters were evaluated.

1) Electrolyte Balance

Sodium, potassium, chloride, calcium, magnesium and phosphorus ion concentrations in serum of patients (n=299) were measured before, and at 6, 12, 18, 24, 30, 36, 48 and 50 weeks after the start of the Compound A treatment.

The laboratory standard values for the panel of electrolytes were taken from the normal reference ranges for the central laboratory.

2) Severity of Constipation, 3) Abdominal Bloating and 4) Abdominal Discomfort

Each parameter (Severity of Constipation, Abdominal bloating or Abdominal discomfort) was evaluated on the scale of: 0 (absent), 1 (mild), 2 (moderate), 3 (severe) and 4 (very severe) in the patients during 6 months (n=246) or 12 months (n=304) treatments.

(Results)

1) Electrolyte Balance

As shown in Table 1, treatment with compound A had no effect on sodium, potassium, chloride, calcium, magnesium and phosphorus ion concentration in serum of the patients. The results demonstrate that Compound A does not induce substantial shift of electrolyte over long-term administration.

TABLE 1

Mean Serum Chemistry Results

| Week | Sodium (mmol/L) | Potassium (mmol/L) | Chloride (mmol/L) | Calcium (mg/dL) | Magnesium (mg/dL) | Phosphorus (mg/dL) |
|---|---|---|---|---|---|---|
| 0 | 141.00 | 4.28 | 103.08 | 9.61 | 2.18 | 3.65 |
| 6 | 142.25 | 4.28 | 103.00 | 9.90 | 2.23 | 3.20 |
| 12 | 139.78 | 4.20 | 103.08 | 9.71 | 2.24 | 3.57 |
| 18 | 141.50 | 4.40 | 105.50 | 9.30 | 2.35 | 3.55 |
| 24 | 139.21 | 4.19 | 102.56 | 9.77 | 2.21 | 3.61 |
| 30 | 136.00 | 4.30 | 100.00 | 9.10 | 2.30 | 2.50 |
| 36 | 138.94 | 4.18 | 102.51 | 9.67 | 2.19 | 3.58 |
| 48 | 139.59 | 4.20 | 102.88 | 9.66 | 2.14 | 3.50 |
| 50 | 139.11 | 4.49 | 102.67 | 9.47 | 2.31 | 3.54 |
| Laboratory Standard | 135-148 | 3.5-5.5 | 96-109 | 8.5-10.6 | 1.6-2.6 | * |

*Female: 15-19 year 2.5-5.3 mg/dL, ≥20 year 2.5-4.5 mg/dL
Male: 15-19 year 2.5-5.6 mg/dL, ≥20 year 2.5-4.5 mg/dL 2) Severity of Constipation (6 and 12 months), 3) Abdominal bloating (6 and 12 months) and 4) Abdominal discomfort (6 and 12 months) were shown in FIG. 1 to FIG. 6 respectively.

As shown in FIGS. 1 to 6, Compound A is effective during the 6 months and 12 months treatment.

Example 2

(Method)

Multi-center, double-blind, randomized, placebo-controlled study was performed to assess post-treatment response, in a portion of the total population, after four (4) weeks of active treatment (48 μg Compound A total daily dose) and three (3) weeks randomized withdrawal period. Patients who demonstrated history of chronic constipation for at least 6 months (having less then three SBMs per week) and at least one associated symptom such as hard stools, incomplete evacuation, straining were enrolled. After 14-day drug-free washout period, they received orally 48 μg (total daily dose) of Compound A for 28 days followed by either 0 or 48 μg (total daily dose) of Compound A for 21 days.

In this study, the following parameters were evaluated.
1) Bowel movements per week
2) Abdominal bloating
3) Abdominal discomfort
4) Severity of Constipation
5) Straining
6) Consistency Each parameter (Abdominal bloating, Abdominal discomfort, Severity of Constipation or Straining) was evaluated on the scale of: 0 (absent), 1 (mild), 2 (moderate), 3 (severe) and 4 (very severe) in the patients. Consistency was evaluated on a scale of: 0 (very loose), 1 (loose), 2 (normal), 3 (hard) and 4 (very hard, little balls)

(Results)

1) Bowel movements per week, 2) Abdominal bloating, 3) Abdominal discomfort, 4) Severity of Constipation, 5) Straining and 6) Consistency were shown in FIG. 7 to FIG. 12 respectively.

As shown in FIGS. 7 to 12, substantially no rebound effect after the discontinuation of the treatment with Compound A was observed, and the efficacy of the compound A was sustained even after stopping the treatment.

This result indicates that the quality of life of the patients is improved by the administration of compound A.

Example 3

(Method)

Patients with irritable bowel syndrome (IBS) were treated with 48 μg of Compound A (24 μg of Compound A b.i.d) for 48 weeks.

In this study, we evaluated the following parameters.
1) Abdominal discomfort
2) Abdominal bloating
3) Severity of Constipation Each of Abdominal discomfort and Abdominal bloating was evaluated on a scale of: 0 (absent), 1 (mild), 2 (moderate), 3 (severe) and 4 (very severe) in the patients. Severity of Constipation was evaluated on a scale of: 0 (very loose), 1: (loose), 2: (normal), 3 (hard), 4 (very hard) in the patients.

(Results)

1) Abdominal discomfort, 2) Abdominal bloating and 3) Severity of Constipation were shown in Table 2 to Table 4 respectively.

As shown in Tables 2 to 4, Compound A is effective during the 12 months treatment in IBS patients.

TABLE 2

Analysis of Abdominal discomfort

| Week | Compound A Mean ± SD (N) Median Range | Compound A Mean ± SD (N) Median Range p-Value* |
|---|---|---|
| Baseline | 1.95 ± 0.850 (183) 2.00 0.00-4.00 | Change from Baseline |
| Week 12 | 1.16 ± 0.836 (135) 1.00 0.00-4.00 | −0.79 ± 0.993 (135) −1.00 −3.00-2.00 <0.001# |
| Week 18 | 0.98 ± 0.874 (111) 1.00 0.00-3.00 | −0.97 ± 1.031 (111) −1.00 −4.00-3.00 <0.001# |
| Week 24 | 1.09 ± 0.917 (107) 1.00 0.00-4.00 | −0.82 ± 1.035 (107) −1.00 −4.00-3.00 <0.001# |
| Week 36 | 0.93 ± 0.799 (57) 1.00 0.00-3.00 | −0.77 ± 0.926 (57) −1.00 −4.00-2.00 <0.001# |
| Week 48 | 0.87 ± 0.929 (52) 1.00 0.00-4.00 | −0.81 ± 0.908 (52) −1.00 −2.00-2.00 <0.001# |
| End of Treatment | 1.28 ± 1.020 (183) 1.00 0.00-4.00 | −0.66 ± 1.112 (183) −1.00 −4.00-2.00 <0.001# |
| Follow-Up | 1.40 ± 0.996 (121) 1.00 0.00-4.00 | −0.55 ± 1.080 (121) −1.00 −4.00-2.00 <0.001# |

*P-value is from a Wilcoxon signed-rank test.

TABLE 3

Analysis of Abdominal bloating

| Week | Compound A Mean ± SD (N) Median Range | Compound A Mean ± SD (N) Median Range p-Value* |
|---|---|---|
| Baseline | 2.23 ± 0.927 (183) 2.00 0.00-4.00 | Change from Baseline |
| Week 12 | 1.43 ± 0.919 (135) 1.00 0.00-4.00 | −0.84 ± 1.045 (135) −1.00 −3.00-3.00 <0.001# |
| Week 18 | 1.19 ± 0.837 (111) 1.00 0.00-3.00 | −1.07 ± 1.068 (111) −1.00 −3.00-3.00 <0.001# |
| Week 24 | 1.26 ± 0.915 (107) 1.00 0.00-4.00 | −0.95 ± 1.102 (107) −1.00 −4.00-3.00 <0.001# |
| Week 36 | 1.05 ± 0.854 (57) 1.00 0.00-3.00 | −1.00 ± 1.134 (57) −1.00 −4.00-2.00 <0.001# |
| Week 48 | 1.12 ± 0.832 (52) 1.00 0.00-4.00 | −0.94 ± 0.802 (52) −1.00 −3.00-1.00 <0.001# |
| End of Treatment | 1.50 ± 1.005 (183) 1.00 0.00-4.00 | −0.73 ± 1.075 (183) −1.00 −4.00-2.00 <0.001# |

TABLE 3-continued

Analysis of Abdominal bloating

| Week | Compound A<br>Mean ± SD (N)<br>Median Range | Compound A<br>Mean ± SD (N)<br>Median Range p-Value* |
|---|---|---|
| Follow-Up | 1.55 ± 0.957 (121)<br>2.00<br>0.00-4.00 | −0.69 ± 1.109 (121)<br>−1.00<br>−3.00-3.00<br><0.001# |

*P-value is from a Wilcoxon signed-rank test.

TABLE 4

Analysis of Severity of Constipation

| Week | Compound A<br>Mean ± SD (N)<br>Median Range | Compound A<br>Mean ± SD (N)<br>Median Range p-Value* |
|---|---|---|
| Baseline | 2.95 ± 0.751 (183)<br>3.00<br>1.00-4.00 | Change from<br>Baseline |
| Week 12 | 1.76 ± 1.003 (135)<br>2.00<br>0.00-4.00 | −1.16 ± 1.099 (135)<br>−1.00<br>−4.00-2.00<br><0.001# |
| Week 18 | 1.33 ± 0.985 (111)<br>1.00<br>0.00-4.00 | −1.59 ± 1.148 (111)<br>−2.00<br>−4.00-3.00<br><0.001# |
| Week 24 | 1.50 ± 0.965 (107)<br>1.00<br>0.00-4.00 | −1.40 ± 1.036 (107)<br>−1.00<br>−3.00-2.00<br><0.001# |
| Week 36 | 1.39 ± 0.921 (57)<br>1.00<br>0.00-4.00 | −1.33 ± 1.123 (57)<br>−1.00<br>−4.00-2.00<br><0.001# |
| Week 48 | 1.37 ± 0.894 (51)<br>1.00<br>0.00-3.00 | −1.37 ± 1.095 (51)<br>−1.00<br>−3.00-1.00<br><0.001# |
| End of Treatment | 1.84 ± 1.120 (183)<br>2.00<br>0.00-4.00 | −1.11 ± 1.148 (183)<br>−1.00<br>−4.00-2.00<br><0.001# |
| Follow-Up | 2.07 ± 0.946 (121)<br>2.00<br>0.00-4.00 | −0.88 ± 1.122 (121)<br>−1.00<br>−4.00-2.00<br><0.001# |

*P-value is from a Wilcoxon signed-rank test.

Example 4

(Method)

Multi-center, parallel-group, double-blind, placebo-controlled study was performed to compare the effect of Compound A on the weekly number of spontaneous bowel movements in male and female patients. Male and female patients with occasional constipation were received 48 µg (total daily dose) of Compound A (24 µg of Compound A b.i.d) for 4 weeks. The bowel movements in the patient were recorded during the treatment.

(Results)

Figure 13:
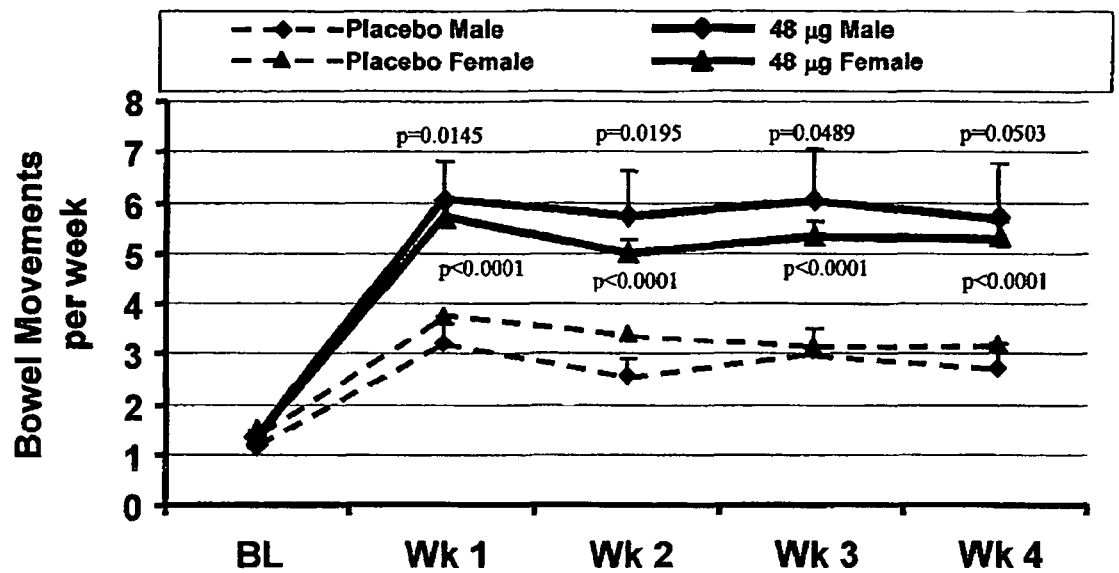
FIG. 13 is a graph showing effects on male vs. female patients in bowel movement.

The effect of 48 µg of Compound A on the weekly number of spontaneous bowel movements in male vs. female patients is shown in FIG. 13.

As shown in FIG. 13, Compound A was significantly effective for both male and female patients. There was no significant difference between the effects in male and female patients.

Example 5

(Method)

Multi-center, parallel-group, double-blind, placebo-controlled study was performed to compare the effect of Compound A on improving weekly number of spontaneous bowel movements among different aged patients with occasional constipation. The patients were received 48 µg (total daily dose) of Compound A (24 µg of Compound A b.i.d) for 4 weeks. The bowel movements in the patient were recorded during the treatment.

(Results)

Figure 14:
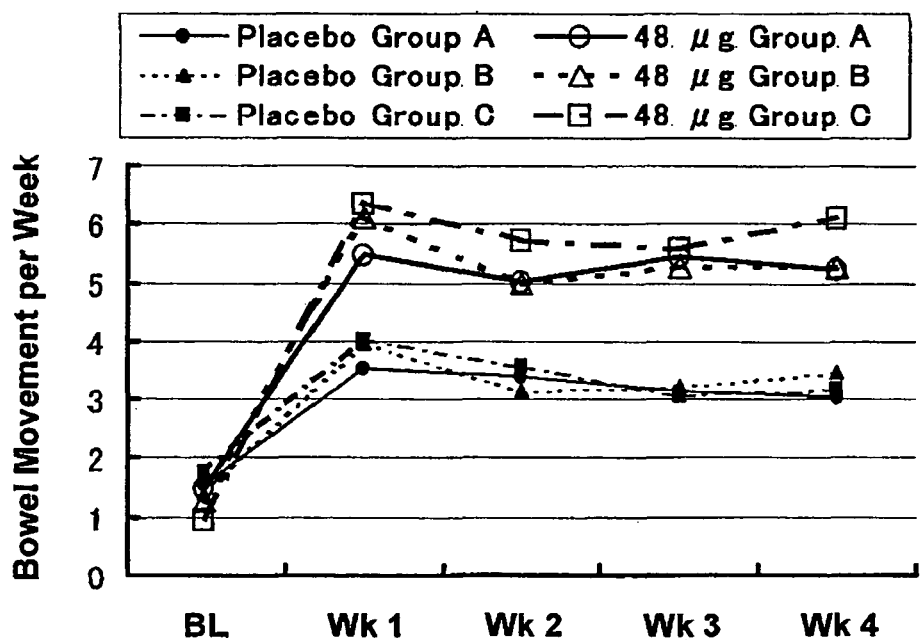
FIG. 14 is a graph showing effects by age in bowel movement.

The result is shown in FIG. 14. As shown in FIG. 14, Compound A was significantly effective in all aged groups, and even 65 years and older patients.

Example 6

(Method)

A 48-week multi-center study was performed to assess the safety and efficacy of 48 µg (total daily dose) of Compound A to subjects with occasional constipation. Patients who demonstrated history of constipation for at least 3 months (having less then three SBMs per week) and at least one associated symptom such as hard stools, incomplete evacuation, straining were enrolled. After 14-day drug-free washout period, they received orally 48 µg of Compound A (24 µg of Compound 1, b.i.d) daily for 48 weeks.

The subjects completed the Medical Outcomes Study (MOS) 36-item short form (SF-36), i.e., a conventionally used QOL assessment form, at enrollment (baseline) and end of treatment (Week 48). Components of the MOS SF-36 (Med Care 30(6),473-483, 1992) are outlined below:

Physical component: Physical Function; Role-Physical, Bodily Pain and General Health Mental component: Vitality, Social Function, Role-Emotional and Mental Health Each of the 8 components was scored within the guidelines of the publisher, including the publisher's guidelines for imputing missing variables. The change from baseline in each of the 8 component scores at the end of treatment (Week 48) were recorded and evaluated with paired t-tests.

(Results)

As shown in Table 5, for each of the 8 component scores, the mean baseline score was between 47 and 52, indicating that the subject population was generally healthy. The mean change from baseline for each component score at Week 48 represented a small increase, which is indicative of an improvement in the respective categories. Improvements that were significantly different from zero were observed at Week 48 for the components of Physical Function, Role-Physical, Bodily Pain, General Health, Vitality, Social Function and Mental Health. The results indicate that Compound A improves the QOL of the patients.

TABLE 5

Summary of SF36 results

| | Component/Scale Score | | | | | | | |
|---|---|---|---|---|---|---|---|---|
| | Physical Function | Role-Physical | Bodily Pain | General Health | Vitality | Social Function | Role-Emotional | Mental Health |
| Baseline | | | | | | | | |
| N | 320 | 320 | 319 | 319 | 319 | 320 | 319 | 319 |
| Mean | 49.04 | 49.75 | 47.53 | 51.52 | 50.61 | 50.12 | 49.52 | 50.60 |
| (Std) | 9.817 | 9.457 | 9.765 | 9.069 | 9.940 | 9.778 | 9.973 | 9.829 |
| Week 48[a] | | | | | | | | |
| N | 153 | 153 | 151 | 151 | 151 | 152 | 151 | 151 |
| Mean [b] | 2.48** | 1.95** | 3.38** | 1.47* | 2.89** | 2.22** | 1.22 | 1.97** |
| (Std) | 8.431 | 7.403 | 9.883 | 7.827 | 9.163 | 8.973 | 9.560 | 9.201 |

[a] Values represented at Week 48 are for the changes from baseline.
[b] *p < 0.05, **P < 0.01 (paired T-tests.)

Example 7

(Method)

A 12-week, double-blind, randomized study was performed to assess the safety and efficacy of oral 16 μg, 32 μg and 48 μg (total daily dose) of compound A to subjects with irritable bowel syndrome (IBS).

The patients answered the IBS QOL questionnaire at baseline, at week 4, Week 12 and at the end of study, and Questionnaire results were scored according to the IBS QOL User's Manual (A Quality of Life Measure for Persons with Irritable Bowel Syndrome (IBS-QOL): User's Manual and Scoring Diskette for United States Version. Seattle, Wash.: University of Washington; 1997). Scaled scores were used for all analyses, and scores were calculated according to the User's Manual as follows:

Scaled Score=([Sum of IBS-QOL items−lowest possible score]/Possible raw score range))×100

Changes from baseline at week 4, week 12 and at the End of Study were assessed for the mean overall score and for the mean domain scores (dysphoria, interference with activity, body image, health worry, food avoidance, social reaction, sexual, and relationship).

(Results)

A summary of mean change from baseline in IBS-QOL scores analyzed without LOCF (Last observation carried forward) is shown in Table 6 to Table 8.

These data indicated that the change from baseline was significantly different from Zero in all groups. In general, the 16 μg of compound A group showed the greatest improvement from baseline of all the groups in every specific area and for QOL overall.

TABLE 6

Summary of change from Baseline in IBS QOL (16 μg)

| | Component/Scaled Score | | | | | | | | |
|---|---|---|---|---|---|---|---|---|---|
| | QOL Overall | Dysphoria | Interference with Activity | Body Image | Health Worry | Food Avoidance | Social Reaction | Sexual | Relationship |
| Baseline | | | | | | | | | |
| N | 51 | 51 | 51 | 51 | 51 | 51 | 51 | 51 | 51 |
| Mean | 55.66 | 53.19 | 65.82 | 41.42 | 37.74 | 46.08 | 63.97 | 64.95 | 67.81 |
| (Std) | 21.165 | 27.333 | 22.544 | 22.877 | 23.113 | 30.016 | 24.546 | 33.913 | 25.387 |
| Week 4 | | | | | | | | | |
| N | 45 | 45 | 45 | 45 | 45 | 45 | 45 | 45 | 45 |
| Mean | 14.7** | 17.85** | 10.87** | 16.39** | 22.41** | 13.89** | 11.94** | 13.33** | 10.74** |
| (Std) | 14.842 | 18.483 | 14.899 | 19.867 | 20.241 | 22.332 | 19.439 | 25.057 | 17.463 |
| Week 12 | | | | | | | | | |
| N | 42 | 42 | 42 | 42 | 42 | 42 | 42 | 42 | 42 |
| Mean | 18.54** | 23.51** | 13.95** | 22.32** | 23.81** | 15.28** | 14.58** | 16.67** | 15.47** |
| (Std) | 17.698 | 20.949 | 18.392 | 21.701 | 22.129 | 26.792 | 21.548 | 29.82 | 21.897 |
| End of Study | | | | | | | | | |
| N | 49 | 49 | 49 | 49 | 49 | 49 | 49 | 49 | 49 |
| Mean | 16.82** | 21.62** | 11.95** | 20.41** | 21.94** | 13.95** | 13.78** | 14.03** | 14.28** |
| (Std) | 17.145 | 20.451 | 18.348 | 21.491 | 21.562 | 25.762 | 20.57 | 28.485 | 20.692 |

TABLE 7

Summary of change from Baseline in IBS QOL (32 μg)

| | Component/Scale Score | | | | | | | | |
|---|---|---|---|---|---|---|---|---|---|
| | QOL Overall | Dysphoria | Interference with Activity | Body Image | Health Worry | Food Avoidance | Social Reaction | Sexual | Relationship |
| Baseline | | | | | | | | | |
| N | 49 | 49 | 49 | 49 | 49 | 49 | 49 | 49 | 49 |
| Mean | 60.14 | 59.69 | 69.82 | 43.37 | 44.38 | 52.21 | 66.84 | 68.62 | 70.23 |
| (Std) | 22.05 | 24.79 | 23.385 | 24.387 | 24.672 | 32.175 | 28.562 | 31.367 | 23.385 |
| Week 4 | | | | | | | | | |
| N | 36 | 36 | 36 | 36 | 36 | 36 | 36 | 36 | 36 |
| Mean | 11.25** | 14.58** | 7.04* | 15.28** | 16.9** | 8.33* | 9.9** | 8.68** | 7.64* |
| (Std) | 16.277 | 20.39 | 17.753 | 18.264 | 17.534 | 23.988 | 16.46 | 18.131 | 18.831 |
| Week 12 | | | | | | | | | |
| N | 33 | 33 | 33 | 33 | 33 | 33 | 33 | 33 | 33 |
| Mean | 13.08** | 15.25** | 9.42** | 17.99** | 19.44** | 11.36** | 10.8** | 10.98** | 9.09* |
| (Std) | 13.527 | 15.285 | 18.052 | 15.21 | 21.616 | 23.46 | 14.173 | 18.424 | 20.87 |
| End of Study | | | | | | | | | |
| N | 44 | 44 | 44 | 44 | 44 | 44 | 44 | 44 | 44 |
| Mean | 12.58** | 14.77** | 8.2** | 17.47** | 17.61** | 10.79** | 11.08** | 10.23** | 10.79** |
| (Std) | 12.621 | 14.429 | 16.726 | 15.344 | 22.317 | 21.906 | 14.32 | 16.894 | 20.139 |

TABLE 8

Summary of change from Baseline in IBS QOL (48 μg)

| | Component/Scaled Score | | | | | | | | |
|---|---|---|---|---|---|---|---|---|---|
| | QOL Overall | Dysphoria | Interference with Activity | Body Image | Health Worry | Food Avoidance | Social Reaction | Sexual | Relationship |
| Baseline | | | | | | | | | |
| N | 45 | 45 | 45 | 45 | 45 | 45 | 45 | 45 | 45 |
| Mean | 59.85 | 56.81 | 68.25 | 45.69 | 44.07 | 50.37 | 66.81 | 71.94 | 75.18 |
| (Std) | 21.664 | 26.802 | 23.396 | 21.396 | 23.274 | 31.927 | 27.074 | 30.404 | 22.365 |
| Week 4 | | | | | | | | | |
| N | 34 | 34 | 34 | 34 | 34 | 34 | 34 | 34 | 34 |
| Mean | 12.43** | 17.28** | 9.14** | 13.24** | 19.61** | 12.01** | 8.82** | 8.46** | 6.87** |
| (Std) | 11.619 | 16.842 | 14.477 | 13.568 | 18.562 | 19.59 | 14.028 | 15.607 | 12.558 |
| Week 12 | | | | | | | | | |
| N | 30 | 30 | 30 | 30 | 30 | 30 | 30 | 30 | 30 |
| Mean | 14.8 | 20.83 | 10.95 | 17.08 | 23.33 | 11.39 | 14.17 | 5 | 6.95 |
| (Std) | 13.65 | 18.863 | 15.091 | 18.419 | 18.098 | 22.153 | 21.143 | 18.159 | 12.202 |
| End of Study | | | | | | | | | |
| N | 43 | 43 | 43 | 43 | 43 | 43 | 43 | 43 | 43 |
| Mean | 11.54** | 16.28** | 7.97** | 14.24** | 17.05** | 8.33** | 12.06** | 3.49 | 6.01** |
| (Std) | 13.002 | 18.62 | 14.387 | 17.43 | 19.067 | 20.002 | 18.72 | 17.535 | 12.244 |

*P < 0.05,
**P < 0.01 (paired T-Tests)

The description of the invention is merely exemplary in nature and, thus, variations that do not depart from the gist of the invention are intended to be within the scope of the invention. Such variations are not to be regarded as a departure from the spirit and scope of the invention.

All patents and publications cited in this specification are herein incorporated by reference

What is claimed is:

1. A method for the long term treatment of chronic constipation in a human subject, wherein the treatment comprises administering to the subject in need thereof an effective amount of a prostaglandin compound represented by Formula (I) and/or its tautomer:

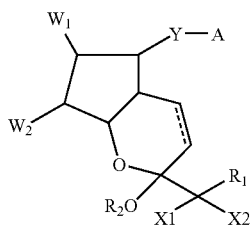 (I)

wherein $W_1$ is =O; and $W_2$ is

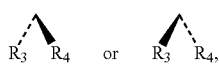

wherein $R_3$ and $R_4$ are hydrogen;
$X_1$ and $X_2$ are halogen;
$R_2$ is hydrogen or alkyl;
Y is a saturated or unsaturated $C_{2-10}$ hydrocarbon chain;
A is —COOH or its salt, ester or amide;
R1 is a saturated or unsaturated, straight chain or branched chain lower hydrocarbon;
the bond between C-13 and C-14 positions is double or single bond, and
the steric configuration at C-15 position is R, S or a mixture thereof,
wherein said prostaglandin compound is administered for over 4 weeks,
wherein the treatment induces substantially no serum electrolyte shifting during the term of treatment,
wherein the amount of said prostaglandin compound to be administered is in the range of about 6-48 µg per day, and
wherein the treatment improves quality of life of the subject.

2. The method of claim 1, wherein said prostaglandin compound is a monocyclic tautomer of formula (I).

3. The method of claim 1, wherein the amount of said prostaglandin compound to be administered is in the range of about 6-32 µg per day.

4. The method of claim 1, wherein the amount of said prostaglandin compound to be administered is in the range of about 6-16 µg per day.

5. The method of claim 1, wherein the amount of said prostaglandin compound to be administered is in the range of about 8-48 µg per day.

6. The method of claim 1, wherein the prostaglandin compound is administered orally.

7. The method of claim 6, wherein said prostaglandin compound is administered with an oil solvent as an excipient.

8. The method of claim 7, wherein said oil solvent is a medium chain fatty acid triglyceride.

9. The method of claim 1, wherein A is —COOH; Y is $(CH_2)_6$; atoms; $R_2$ is hydrogen atom; $X_1$ and $X_2$ are fluorine atoms; and $R_1$ is $(CH_2)_3CH_3$.

10. The method of claim 1, wherein said prostaglandin compound is administered for at least 6 months.

11. The method of claim 1, wherein said prostaglandin compound is administered for at least 1 year.

12. The method of claim 1, wherein said human subject is a male human subject.

13. The method of claim 1, wherein said human subject is a human subject aged 65 years and older.

14. The method of claim 1, wherein A is —COOH; Y is $(CH_2)_6$; atoms; $R_2$ is hydrogen atom; $X_1$ and $X_2$ are fluorine atoms; and $R_1$ is $CH_2CH(CH_3)CH_2CH_3$.

15. The method of claim 1, wherein said human subject is aged 18 years or older.

16. The method of claim 1, wherein said prostaglandin compound is administered for at least 2 months.

17. The method of claim 1, wherein the treatment improves quality of life of the subject that is confirmed by SF-36.

* * * * *